(12) United States Patent
Brockway et al.

(10) Patent No.: US 8,740,789 B2
(45) Date of Patent: Jun. 3, 2014

(54) AUTOMATIC ETIOLOGY SEQUENCING SYSTEM AND METHOD

(75) Inventors: Marina Brockway, Shoreview, MN (US); David Johnson, Inver Grove Heights, MN (US); Don Goscha, Elk River, MN (US); Veerichetty A. Kadhiresan, Centerville, MN (US); Muralidharan Srivathsa, Shoreview, MN (US); Lisa Haeder, New Hope, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1754 days.

(21) Appl. No.: 11/071,646

(22) Filed: Mar. 3, 2005

(65) Prior Publication Data

US 2006/0200007 A1    Sep. 7, 2006

(51) Int. Cl.
| | | |
|---|---|---|
| *A61B 5/00* | (2006.01) | |
| *G06N 3/02* | (2006.01) | |
| *G06N 3/04* | (2006.01) | |
| *G06Q 50/24* | (2012.01) | |
| *G06F 19/00* | (2011.01) | |
| *G06N 3/00* | (2006.01) | |
| *G06Q 50/00* | (2012.01) | |

(52) U.S. Cl.
CPC ............... *G06F 19/345* (2013.01); *G06F 19/34* (2013.01); *G06F 19/32* (2013.01); *G06F 19/30* (2013.01); *G06F 19/3418* (2013.01); *G06F 19/3487* (2013.01); *G06F 19/363* (2013.01); *G06F 19/3406* (2013.01); *G06N 3/02* (2013.01); *G06N 3/0427* (2013.01); *G06Q 50/24* (2013.01); *A61B 5/0022* (2013.01); *A61B 5/0002* (2013.01); *A61B 5/686* (2013.01); *Y10S 128/92* (2013.01); *Y10S 128/924* (2013.01); *Y10S 128/925* (2013.01); *Y10S 706/924* (2013.01)

USPC ........... 600/300; 600/301; 128/920; 128/924; 128/925; 705/2; 705/3; 706/45; 706/16; 706/21; 706/924; 702/19; 707/705; 707/722; 607/4; 607/5; 607/6; 607/18; 607/60

(58) Field of Classification Search
CPC ........ G06N 3/02; G06N 3/0247; G06F 19/34; G06F 19/36; G06F 19/363; G06F 19/3487; G06F 19/3418; G06F 19/345; G06Q 50/24; A61B 5/0002; A61B 5/0022
USPC ........... 600/300–301; 705/2–4; 128/903–905, 128/920–925; 340/573.1–576; 379/106.1–106.2; 706/45–47, 21, 924, 706/15–16; 702/19

See application file for complete search history.

(56) References Cited

U.S. PATENT DOCUMENTS

| 5,193,535 A | 3/1993 | Bardy et al. |
| 5,257,621 A | 11/1993 | Bardy et al. |

(Continued)

*Primary Examiner* — Bill Thomson
*Assistant Examiner* — Marie Archer
(74) *Attorney, Agent, or Firm* — Schwegman Lundberg & Woessner, P.A.

(57) ABSTRACT

A system and related method for identifying a trigger event to a patient health-related exacerbation. The system includes at least one sensor configured to collect data related to the patient health-related exacerbation, an analyzer configured to validate the collected data, a patient interface device configured to receive patient inputs to at least one question, and an identifier device configured to receive the patient inputs and collected data and identify the trigger event. The system may also include an expert system configured to receive the patient inputs and the validated collected data and identify a primary patient disease, and a reporting device configured to generate reports related to the identified primary patient disease, patient inputs, and sensed patient conditions.

26 Claims, 6 Drawing Sheets

(56) References Cited

U.S. PATENT DOCUMENTS

| | | | |
|---|---|---|---|
| 5,724,025 A * | 3/1998 | Tavori | 340/573.1 |
| 6,336,903 B1 | 1/2002 | Bardy | |
| 6,368,284 B1 | 4/2002 | Bardy | |
| 6,398,728 B1 | 6/2002 | Bardy | |
| 6,411,840 B1 | 6/2002 | Bardy | |
| 6,440,066 B1 | 8/2002 | Bardy | |
| 6,527,712 B1 * | 3/2003 | Brown et al. | 600/300 |
| 6,607,482 B1 * | 8/2003 | Teitelbaum | 600/300 |
| 6,671,547 B2 | 12/2003 | Lyster et al. | |
| 6,687,685 B1 * | 2/2004 | Sadeghi et al. | 706/15 |
| 6,694,186 B2 | 2/2004 | Bardy | |
| 6,704,595 B2 | 3/2004 | Bardy | |
| 6,712,763 B2 * | 3/2004 | Abraham-Fuchs et al. | 600/300 |
| 6,754,528 B2 | 6/2004 | Bardy et al. | |
| 6,755,783 B2 * | 6/2004 | Cosentino et al. | 600/300 |
| 6,811,537 B2 | 11/2004 | Bardy | |
| 6,826,425 B2 | 11/2004 | Bardy | |
| 6,827,690 B2 | 12/2004 | Bardy | |
| 6,834,203 B2 | 12/2004 | Bardy | |
| 6,904,312 B2 | 6/2005 | Bardy | |
| 6,908,437 B2 | 6/2005 | Bardy | |
| 6,913,577 B2 | 7/2005 | Bardy | |
| 6,951,539 B2 | 10/2005 | Bardy | |
| 7,056,289 B2 * | 6/2006 | Kasper et al. | 600/300 |
| 7,117,028 B2 | 10/2006 | Bardy | |
| 7,117,185 B1 * | 10/2006 | Aliferis et al. | 706/12 |
| 7,191,106 B2 * | 3/2007 | Minor et al. | 703/2 |
| 7,213,009 B2 * | 5/2007 | Pestotnik | 706/46 |
| 7,853,456 B2 * | 12/2010 | Soto et al. | 705/2 |
| 2002/0169367 A1 | 11/2002 | Bardy | |
| 2002/0184177 A1 * | 12/2002 | Abraham-Fuchs et al. | 706/47 |
| 2002/0188213 A1 * | 12/2002 | Bardy | 600/509 |
| 2003/0149597 A1 * | 8/2003 | Zaleski | 705/2 |
| 2003/0233031 A1 * | 12/2003 | Rice | 600/300 |
| 2004/0039263 A1 | 2/2004 | Bardy | |
| 2004/0122702 A1 * | 6/2004 | Sabol et al. | 705/2 |
| 2004/0127958 A1 | 7/2004 | Mazar et al. | |
| 2004/0193064 A1 * | 9/2004 | Shusterman | 600/504 |
| 2004/0230127 A1 | 11/2004 | Bardy | |
| 2004/0236237 A1 | 11/2004 | Bardy | |
| 2004/0254613 A1 | 12/2004 | Ostroff et al. | |
| 2005/0015352 A1 * | 1/2005 | Verlinden et al. | 706/45 |
| 2005/0027331 A1 | 2/2005 | Bardy | |
| 2006/0136259 A1 * | 6/2006 | Weiner et al. | 705/2 |

\* cited by examiner

AUTOMATIC ETIOLOGY SEQUENCING SYSTEM AND METHOD

TECHNICAL FIELD

The present invention generally relates to monitoring patients, and more specifically relates to systems and methods for identifying a trigger event to a patient health-related exacerbation and automatically identifying a patient disease.

BACKGROUND

Management of patients with chronic disease consumes a significant proportion of the total health care expenditure in the United States. Many of these diseases are widely prevalent and have significant annual incidences as well. Heart failure prevalence alone is estimated at over 5.5 million patients in 2000 with incidence rates of over half a million additional patients annually, resulting in a total health care burden in excess of $20 billion. Heart failure, like many other chronic diseases such as asthma, COPD, chronic pain, and epilepsy, is event driven, where acute de-compensations result in hospitalization. In addition to causing considerable physical and emotional trauma to the patient and family, event driven hospitalizations consume a majority of the total health care expenditure allocated to the treatment of heart failure. Hospitalization and treatment for an acute de-compensation typically occurs after the de-compensation event has happened. However, most heart failure patients exhibit prior non-traumatic symptoms, such as steady weight gain, in the weeks or days prior to the de-compensation. If the caregiver is aware of these symptoms, it is possible to intervene before the event, at substantially less cost to the patient and the health care system. Intervention is usually in the form of a re-titration of the patient's drug cocktail, reinforcement of the patient's compliance with the prescribed drug regimen, or acute changes to the patient's diet and exercise. Such intervention is usually effective in preventing the de-compensation episode and thus avoiding hospitalization. Patients with chronic heart disease can receive implantable cardiac devices such as pacemakers, implantable cardioverter defibrillators (ICDs), and heart failure cardiac resynchronization therapy (CRT) devices.

Currently, the electrophysiologist that implants pacemakers and ICDs requires their patients to make clinic visits periodically, usually once every three or four months, in order to verify if their implanted device is working correctly and programmed optimally. Device follow-ups are usually performed by the nurse-staff assisted by the sales representative from the device manufacturers. Device follow-ups are labor intensive and typically require patients to make multiple clinic visits.

The data the caregiver does receive regarding a patient requires the caregiver to analyze the data and provide predictive and post-event diagnosis based on the data. However, as the amount of data collected regarding a particular patient increases, it becomes more difficult for a caregiver to assimilate and provide a meaningful analysis of all of the data. In addition, it is difficult for a caregiver to identify trends and other information from particular patients and leverage this knowledge for the treatment of larger populations.

Patients with a chronic disease (e.g., heart failure) usually have a number of comorbidities. When the patient's health exacerbates, it may be difficult to identify what triggered the exacerbation from the data provided to the caregiver via the implanted devices or a physical examination of the patient. Since the caregiver is typically responsible for not only treating symptoms related to the exacerbation but also eradicating the primary source of the exacerbation, there is a need for additional resources and information for the caregiver.

It would therefore be desirable to develop an automated system to collect data regarding the physiological condition of a patient, as well as collect data from implanted devices, and to automate the process of analyzing the data available to the caregiver of a patient.

SUMMARY OF THE INVENTION

The present invention generally relates to monitoring patients, and more specifically relates to systems and methods for identifying a trigger event to a patient health-related exacerbation and automatically identifying a patient disease.

One aspect of the invention relates to a system that identifies a trigger event to a patient health-related exacerbation. The system includes at least one sensor configured to collect data related to the patient health-related exacerbation, an analyzer configured to validate the collected data, a patient interface device configured to receive patient inputs to at least one question, and an identifier device configured to receive the patient inputs and collected data and identify the trigger event. The system may also include an expert system configured to receive the patient inputs and the validated collected data and identify a primary patient disease, and a reporting device configured to generate reports related to the identified primary patient disease, patient inputs, and sensed patient conditions.

Another aspect of the invention relates to a method of identifying an exacerbation trigger event in a patient having a chronic illness. The method includes collecting sensor data indicative of at least one patient physical condition, cross-correlating the collected sensor data to validate the collected data, collecting patient responses to an interactive questionnaire, and identifying the exacerbation trigger event based on the collected data and patient responses. The method may also include identifying a primary disease associated with the exacerbation trigger event using an expert system.

A further aspect of the invention relates to a method of automatically identifying a primary patient disease. The method may include the steps of collecting sensor data indicative of at least one patient physical condition, cross-correlating the collected sensor data to validate the collected data, collecting patient responses to an interactive questionnaire, and identifying the primary patient disease using an expert system, the validated collected data, and the patient responses.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE PREFERRED EMBODIMENT

The present system and methods are described generally with respect to an advanced patient management ("APM") system configured to collect patient-specific information, store and collate the information, and generate actionable recommendations to enable the predictive management of patients. The APM system is also configured to leverage a remote communications infrastructure to provide automatic device follow-ups to collect data, coordinate therapy, and to determine if remote devices are functioning properly. More specifically, the APM system is configured to collect data related to a patient, identify a trigger event to a patient health-related exacerbation, and automatically identify a patient disease.

The term "patient" is used herein to mean any individual from whom information is collected. The term "caregiver" is used herein to mean any provider of services, such as health care providers including, but not limited to, nurses, doctors, and other health care provider staff.

Figure 1:
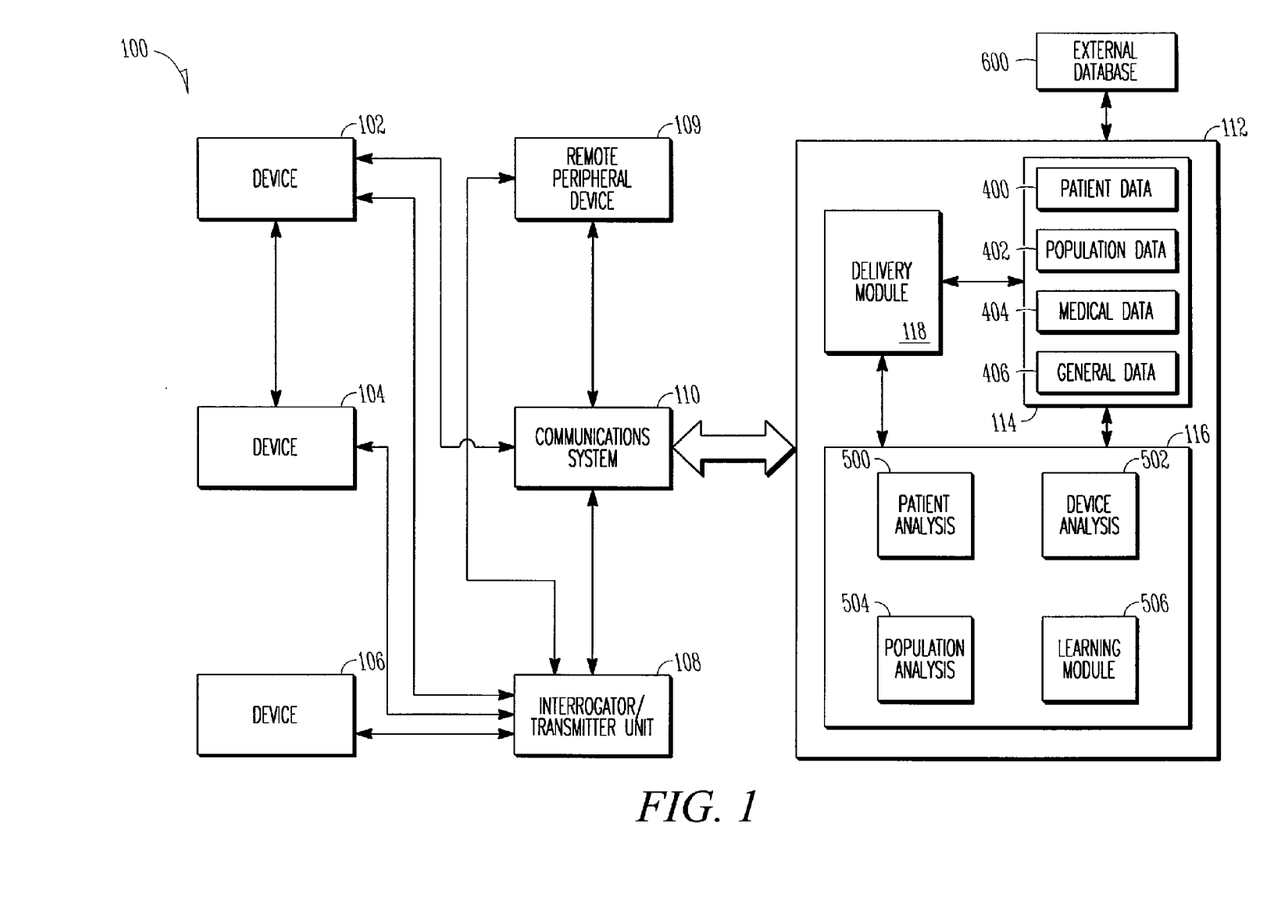
FIG. 1 illustrates an example advanced patient management system made in accordance with the present invention.

FIG. 1 illustrates an example APM system 100 made in accordance with the present invention. APM system 100 generally includes the following components: one or more devices 102, 104, and 106, one or more interrogator/transceiver units 108, a communication system 110, one or more remote peripheral devices 109, and a host 112.

Each component of the APM system 100 can communicate using the communication system 110. Some components may also communicate directly with one another. For example, devices 102 and 104 may be configured to communicate directly with one another. The various components of the example APM system 100 illustrated herein are described below. Additional details related to the features and functionality of APM system 100 can be found in related application Ser. No. 10/330,677, filed Dec. 27, 2002 and entitled: "Advanced Patient Management System Including Interrogator/Transceiver Unit", which application is incorporated herein by reference in its entirety.

I. Devices

Devices 102, 104, and 106 can be implantable devices or external devices that may provide at least one of the following functions with respect to a patient in addition to other possible functions: (1) sensing/measuring, (2) data analysis, (3) therapy, (4) distribution of product, and (5) communication. For example, in one embodiment, devices 102, 104, and 106 are either implanted or external devices used to sense or measure a variety of physiological, subjective, and environmental conditions of a patient using electrical, mechanical, and/or chemical means. The devices 102, 104, and 106 can be configured to automatically gather data or can require manual intervention by the patient. The devices 102, 104, and 106 can be devices that are positioned external and separated from the patient, positioned on an external surface of the patient, or positioned within the patient as an implanted device or sensor. The devices 102, 104, and 106 can be configured to store data related to the physiological and/or subjective measurements and/or transmit the data to the communication system 110 using a variety of methods, described in detail below. Although three devices 102, 104, and 106 are illustrated in the example embodiment shown, more or fewer devices may be used for a given patient.

The devices 102, 104, and 106 can be configured to analyze the measured data and act upon the analyzed data. For example, the devices 102, 104, and 106 are configured to modify therapy or provide alarm indications based on the analysis of the data.

In one embodiment, devices 102, 104, and 106 also provide therapy. Therapy can be provided automatically or in response to an external communication. Devices 102, 104, and 106 are programmable in that the characteristics of their sensing, therapy (e.g., duration and interval), or communication can be altered by communication between the devices 102, 104, and 106 and other components of the APM system 100. Devices 102, 104, and 106 can also perform self-checks or be interrogated by the communication system 110 to verify that the devices are responding properly.

The devices 102, 104, and 106 can be configured to communicate with the patient and with other devices and features of the APM. For example, the devices 102, 104, and 106 can communicate with a patient using sound or visual prompts to, for example, obtain answers to questions, remind the patient to perform certain tasks, and warn the patient about the presence of predetermined threshold trends and conditions that represent the patient's wellbeing. The devices 102, 104, and 106 may also include user interface features such as a keypad, touch control screen, or other input device that facilitate communication between the patient and the devices 102, 104, and 106.

Additional examples of different embodiments of the devices 102, 104, and 106 are provided below.

Devices implanted within the body have the ability to sense and communicate as well as to provide therapy. Implantable devices can provide direct measurement of characteristics of the body, including, without limitation, electrical cardiac activity (e.g., a pacemaker, cardiac resynchronization management device, defibrillator, etc.), physical motion, temperature, heart rate, activity, blood pressure, breathing patterns, ejection fractions, blood viscosity, blood chemistry, blood glucose levels, and other patient-specific clinical physiological parameters, while minimizing the need for patient compliance.

A heart rate sensor, typically found in a pacemaker or defibrillator, is one example of an implantable device. In the heart, an electrical wave activates the heart muscle just prior to contraction. As is known in the art, electrical circuits and lead-wires transduce the heart's activation event and reject other, non-essential electrical events. By measuring the time interval between activation events, the heart rate can be determined. A transthoracic impedance sensor is another example of a sensor in an implantable device. During the respiratory cycle, large volumes of air pass into and out of the body. The electrical resistance of the thorax changes markedly as a result of large differences in conductivity of air and body tissues. The thoracic resistance can be measured during respiration and converted into a measurable electrical signal (i.e., impedance) so that breathing rate and profile can be approximated. Implantable devices can also sense chemical conditions, such as glucose levels, blood oxygen levels, etc. Further, the APM system 100 may utilize other implantable devices as well that provide physiological measurements of the patient, such as drug pumps, neurological devices (e.g., stimulators), oxygen sensors, etc.

Derived measurements can also be determined from the implantable device sensors. For example, a sleep apnea sensor can rely on measurements taken by an implanted accelerometer that measures respiration patterns via an impedance sensor.

The sleep sensor can estimate apnea/hypopnea indices based on the measured hypo/hyperventilation patterns. Other derived measurements include, but are not limited to, a functional capacity indicator, autonomic tone indicator, sleep quality indicator, cough indicator, anxiety indicator, and cardiovascular wellness indicator for calculating a quality of life indicator quantifying a patient's overall health and well-being.

Devices 102, 104, and 106 can also be external devices, or devices that are not implanted in the human body, that are used to measure physiological data. Such devices include a multitude of devices to measure data relating to the human body, such as temperature (e.g., a thermometer), blood pressure (e.g., a sphygmomanometer), blood characteristics (e.g., glucose levels), body weight, physical strength, mental acuity, diet, heart characteristics, and relative geographic position (e.g., a Global Positioning System (GPS)).

Devices 102, 104, and 106 can also be environmental sensors. The devices can be placed in a variety of geographic locations (in close proximity to patient or distributed throughout a population) and record non-patient specific characteristics such as, but not limited to, temperature, air quality, humidity, carbon monoxide level, oxygen level, barometric pressure, light intensity, and sound.

One or more of the devices 102, 104, and 106 (for example, device 106) may be external devices that measure subjective or perceptive data from the patient. Subjective data is information related to a patient's feelings, perceptions, and/or opinions, as opposed to objective physiological data. For example, the "subjective" devices can measure patient responses to inquiries such as "How do you feel?" and "How is your pain?" The device can prompt the patient and record subjective data from the patient using visual and/or audible cues. For example, the patient can press coded response buttons or type an appropriate response on a keypad. Alternatively, subjective data may be collected by allowing the patient to speak into a microphone and using speech recognition software to process the subjective data.

In one example embodiment, the subjective device presents the patient with a relatively small number of responses to each question posed to the patient. For example, the responses available to the patient may include three faces representing feelings of happiness, nominalness, and sadness. Averaged over time, a trend of a patient's well being will emerge from the patient's choices.

The subjective data can be collected from the patient at set times, or, alternatively, collected whenever the patient chooses to provide subjective data. The subjective data can also be collected substantially contemporaneously with physiological data to provide greater insight into overall patient wellness. The subjective device 106 can be any device that accepts input from a patient or other concerned individual and/or provides information in a format that is recognizable to the patient. Device 106 typically includes a keypad, mouse, display, handheld device, interactive TV, cellular telephone or other radio frequency ("RF") communications device, cordless phone, corded phone, speaker, microphone, email message, or physical stimulus.

The APM system 100 may also include one or more remote peripheral devices 109. The remote peripheral device 109 may include, for example and without limitation, cellular telephones, pagers, PDA devices, facsimiles, remote computers, printers, video and/or audio devices, etc. The remote peripheral device 109 can communicate using wired or wireless technologies and may be used by the patient or caregiver to communicate with the communication system 110 and/or the host 112. For example, the remote peripheral device 109 can be used by the caregiver to receive alerts from the host 112 based on data collected from the patient and to send instructions from the caregiver to either the patient or other clinical staff. In another example, the remote peripheral device 109 is used by the patient to receive periodic or real time updates and alerts regarding the patient's health and well-being.

II. Interrogator/Transceiver Unit

Figure 2:
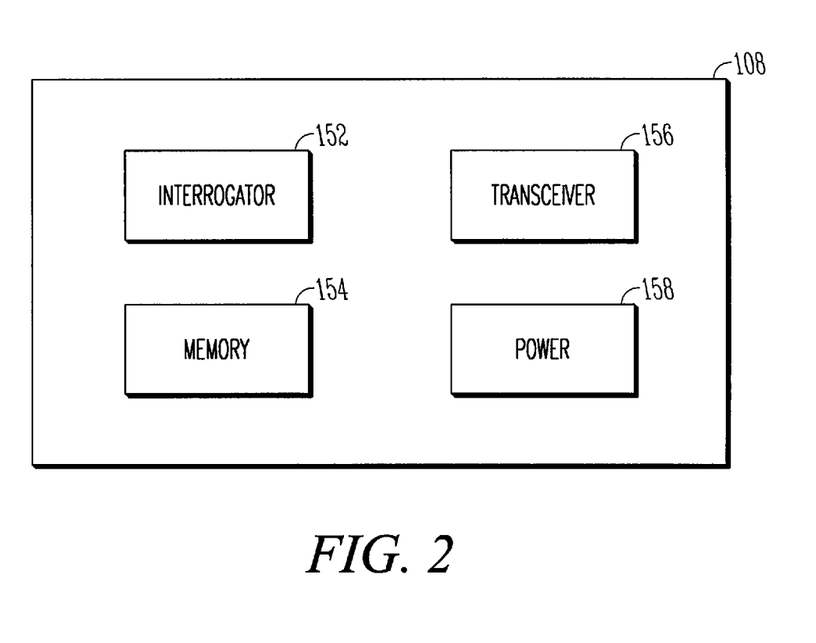
FIG. 2 illustrates an example interrogator/transceiver unit made in accordance with the present invention.

Referring now to FIG. 2, the example APM system 100 includes one or more interrogator/transceiver units ("ITUs"), such as ITU 108. The ITU 108 includes an interrogator module 152 for sending and receiving data from a device, such as devices 102, 104, and 106, a memory module 154 for storing data, a transceiver module 156 for sending and receiving data to and from other components of the APM system 100. The transceiver module may also operate as an interrogator of the devices 102, 104 and 106. The ITU 108 also includes a power module 158 that provides power.

The ITU 108 may perform one or more of the following functions: (1) data storage; (2) data analysis; (3) data forwarding; (4) patient interaction; (5) patient feedback; and (6) data communications. For example, the ITU 108 may facilitate communications between the devices 102, 104, and 106 and the communication system 1 10. The ITU 108 can, periodically or in real-time, interrogate and download into memory clinically relevant patient data from the devices 102, 104, 106. This data includes, in the cardiac sensor context, for example, P and R-wave measurements, pacing, shocking events, lead impedances, pacing thresholds, battery voltage, capacitor charge times, ATR episodes with electrograms, tachycardia episodes with electrograms, histogram information, physiological conditions that represent efficacy and compliance of a drug regimen, and any other clinical information necessary to ensure patient health and proper device function. The data is sent to the ITU 108 by the devices 102, 104, and 106 in real-time or periodically uploaded from buffers in the devices.

The ITU 108 may also allow patient interaction. For example, the ITU 108 may include a patient interface and allow the patient to input subjective data. In addition, the ITU 108 may provide feedback to the patient based on the data that has been analyzed or based on information communicated by the communication system 110.

In another embodiment, the ITU 108 includes a telemetry link from the devices to a network that forms the basis of a wireless LAN in the patient's home. The ITU 108 systematically uploads information from the devices 102, 104, 106 while the patient is sleeping, for example. The uploaded data is transmitted through the communication system 110 or directly to the host 112. In addition, in one embodiment the ITU 108 functions in a hybrid form, utilizing wireless communication when available and defaulting to a local wireless portal or a wired connection when the wireless communication becomes unavailable.

When the interrogator 152 uses radio frequency to communicate with the devices 102, 104, 106, the ITU 108 may be in the form of a small device that is placed in an inconspicuous place within the patient's residence. Alternatively, the ITU 108 may be implemented as part of a commonly used appliance in the patient's residence. For example, the ITU may be integrated with an alarm clock that is positioned near the patient's bed. In another embodiment, the ITU may be implemented as part of the patient's personal computer system. Other embodiments are also possible.

In another embodiment, the ITU 108 may comprise a handheld device such as a PDA, cellular telephone, or other similar device that is in wireless communication with the devices 102, 104, and 106. The hand-held device may upload the data to the communication system 110 wirelessly. Alternatively, the hand-held device may periodically be placed in a cradle or other similar device that is configured to transmit the data to the communication system 110.

ITU 108 may also be capable of performing a variety of self-diagnostic tests on the ITU 108 and APM 100 to verify proper functionality and ensure that communication with the communication system 110 has not been compromised. For example, the ITU 108 can perform a diagnostic loop-back test at a time set by the host 112, which involves sending a request through the communication system 110 to the host 112. The host 112 can then reply with a response back through the communication system 110 to the ITU 108. If a specific duration elapses before the ITU 108 receives the response or the ITU 108 receives an unexpected response, or if the host 112 does not receive the diagnostic test communication, the ITU 108 can provide indications that the system is not functioning properly and the host 112 can alert an operator that there may be compromised communications with that specific ITU 108. For example, if wireless communications between the ITU 108 and the communication system 110 have been interrupted, and the ITU 108 performs a self-diagnostic test that fails, the ITU 108 may alert the patient so that corrective action may be taken. The alert can take the form of a sound or a visual and/or audible enunciator to alert the patient that communication has been interrupted. In another embodiment, the ITU 108 can automatically failback to a wired system to communicate with the communication system 110 and perform the same communications compromise checks.

In other embodiments of the APM system 100, the ITU 108 function can be integrated into devices 102, 104, and 106, so that the devices can communicate directly with the communication system 110 and/or host 112. The devices 102, 104 and 106 can incorporate multi-mode wireless telecommunications such as cellular, BLUETOOTH, or IEEE 802.11B to communicate with the communication system 110 directly or through a local wireless to a wired portal in the patients' home. This is particularly advantageous for devices that are mobile (e.g., an implanted device in a patient that is traveling).

The device 102 can be configured to communicate with the communication system 110 or ITU 108 at given intervals, such as once a week. The device 102 can record data for the time period (e.g., a week) and transmit the data during the portion of the cycle that transmission is active and then conserve energy for the rest of the cycle. In another example, the device 102 conserves energy and only communicates with the communication system 110 when an "interesting" event, such as a heart arrhythmia, has occurred. In this manner, device 102 can communicate directly with the communication system 110 with or without ITU 108, while conserving the energy of the device by communicating only during a given duty cycle.

III. Communication System

Figure 3:
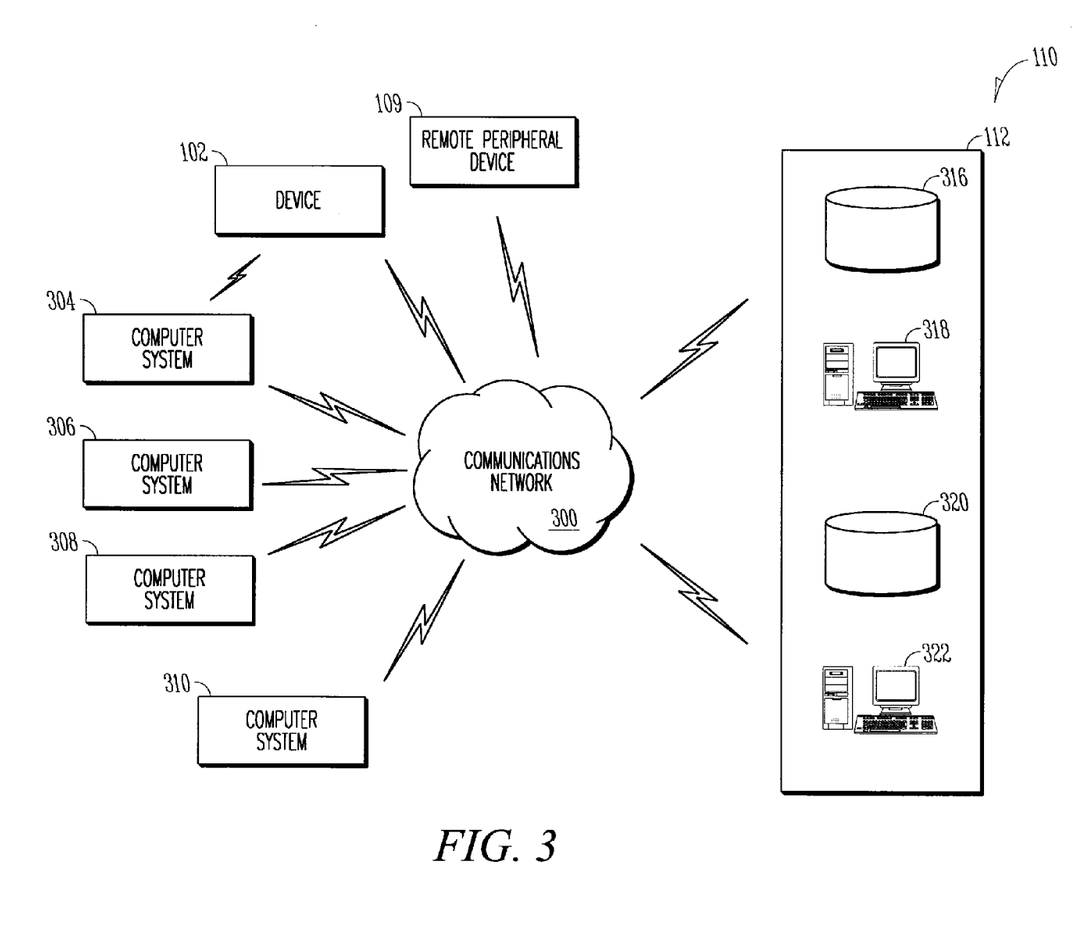
FIG. 3 illustrates an example communication system made in accordance with the present invention.

Communication system 110 provides communication between and among the various components of the APM system 100, such as the devices 102, 104, and 106, host 112, and remote peripheral device 109. FIG. 3 illustrates one embodiment for the communication system 110 made in accordance with the present invention. The communication system 110 includes a plurality of computer systems 304, 306, 308, and 310, as well as device 102, host 112, and remote peripheral device 109, connected to one another by the communication system 300. The communication system 300 may be, for example, a local area network (LAN), wide area network (WAN), or the Internet. Communications among the various components, as described more fully below, may be implemented using wired or wireless technologies.

In the example embodiment illustrated, the host 112 includes server computers 318 and 322 that communicate with computers 304, 306, 308, and 310 using a variety of communications protocols. The server computers 318 and 322 store information in databases 316 and 320. This information may also be stored in a distributed manner across one or more additional servers.

A variety of communication methods and protocols may be used to facilitate communication between devices 102, 104, and 106, ITU 108, communication system 110, host 112, and remote peripheral device 109. For example, wired and wireless communications methods may be used. For any given communication method, a multitude of standard and/or proprietary communication protocols may be used. Further, a combination of two or more of the communication methods and protocols may also be used.

IV. Host

The example host 112 includes a database module 114, an analysis module 116, and a delivery module 118 (see FIG. 1). Host 112 preferably includes enough processing power to analyze and process large amounts of data collected from each patient, as well as to process statistics and perform analysis for large populations. For example, the host 112 may include a mainframe computer or multi-processor workstation. The host 112 may also include one or more personal computer systems containing sufficient computing power and memory. The host 112 may include storage medium (e.g., hard disks, optical data storage devices, etc.) sufficient to store the massive amount of high-resolution data that is collected from the patients and analyzed.

The host 112 may also include identification and contact information (e.g., IP addresses, telephone numbers, or a product serial number) for the various devices communicating with it, such as ITU 108 and peripheral device 109. For example, each ITU 108 is assigned a hard-coded or static identifier (e.g., IP address, telephone number, etc.), which allows the host 112 to identify which patient's information the host 112 is receiving at a given instant. Alternatively, each device 102, 104, and 106 may be assigned a unique identification number, or a unique patient identification number may be transmitted with each transmission of patient data.

Referring again to FIG. 1, the example database module 114 includes a patient database 400, a population database 402, a medical database 404, and a general database 406, all of which are described further below.

The patient database 400 includes patient specific data, including data acquired by the devices 102, 104, and 106. The patient database 400 also includes a patient's medical records, the patient's current health information, targeted health information, and pharmaceutical information. The patient database 400 can include historical information regarding the devices 102, 104, and 106. The information stored in the database 400 can be recorded at various times depending on the patient requirements or device requirements. Alternatively, data in the database 400 can be updated in real time. Typically, the sampling frequency depends on the health condition being monitored and the co-morbidities.

The population database 402 includes non-patient specific data, such as data relating to other patients and population trends. The population database 402 also records epidemic-class device statistics and patient statistics. The population database 402 also includes data relating to staffing by health care providers, environmental data, pharmaceuticals, etc. In some cases, patient information from the patient database 400 may be added to the population database to supplement and maintain currency of the population database information and trends.

The example medical database 404 includes clinical data relating to the treatment of diseases. For example, the medical database 404 includes historical trend data for multiple patients in the form of a record of progression of their disease(s) along with markers of key events.

The general database 406 includes non-medical data of interest to the patient. The general database 406 can include information relating to, for example, news, finances, shopping, technology, entertainment, and/or sports. The general database 406 can be customized to provide general information of specific interest to the patient. For example, stock information can be presented along with the latest health information as detected from the devices 102, 104, and 106.

In another embodiment, information is also provided from an external source, such as external database 600. For example, the external database 600 may include patient electronic medical records; a pharmaceutical database that contains information on pharmacodynamics, drug side effects, drug compatibility; pharmacogenomics; family and personal health or medical history; clinical trials, physician and other guidelines; and environmental databases.

The example analysis module 116 includes a patient analysis module 500, device analysis module 502, population analysis module 504, and learning module 506. Patient analysis module 500 may utilize information collected by the APM system 100, as well as information for other relevant sources, to analyze data related to a patient and provide timely and predictive assessments of the patient's well-being.

In performing analysis, the patient device module 500 may utilize data collected from a variety of sources, include patient specific physiological and subjective data collected by the APM system 100, medical and historical records (e.g., lab test results, histories of illnesses, etc., drugs currently and previously administered, etc.), as well as information related to population trends provided from sources external to the APM system 100.

For example, in one embodiment, the patient analysis module 500 makes a predictive diagnosis of an oncoming event based on information stored in the database module 114. For example, the data continuously gathered from a device of a given patient at a heightened risk for a chronic disease event (such as de-compensations in heart failure) is analyzed. Based on this analysis, therapy, typically device-based or pharmaceutical, is then applied to the patient either through the device or through clinician intervention.

In another example embodiment, the patient analysis module 500 provides a diagnosis of patient health status and predicted trend based on present and recent historical data collected from a device as interpreted by a system of expert knowledge derived from working practices within clinics. For example, the patient analysis module 500 performs probabilistic calculations using currently collected information combined with regularly collected historical information to predict patient health degradation.

In another example embodiment, the patient analysis module 500 may conduct pre-evaluation of the incoming data stream combined with patient historical information and information from patients with similar disease states. The pre-evaluation system is based on data derived from working clinical practices and the records of outcomes. The derived data is processed in a neural network, fuzzy logic system, or equivalent system to reflect the clinical practice. Further, the patient analysis module 500 may also provide means for periodic processing of present and historical data to yield a multidimensional health state indication along with disease trend prediction, next phase of disease progression co-morbidities, and inferences about what other possible diseases may be involved. The patient analysis module 500 may also integrate data collected from internal and external devices with subjective data to optimize management of overall patient health.

Device analysis module 502 analyzes data from the devices 102, 104, and 106 and ITU 108 to predict and determine device issues or failures. For example, if an implanted device 102 fails to communicate at an expected time, device analysis module 502 determines the source of the failure and takes action to restore the performance of the device 102. The device analysis module 502 may also perform additional deterministic and probabilistic calculations. For example, the device analysis module 502 gathers data related to charge levels within a given device, such as an ICD, and provides analysis and alerting functions based on this information if, for example, the charge level reaches a point at which replacement of the device and/or battery is necessary. Similarly, early degradation or imminent failure of implanted devices can be identified and proactively addressed, or at-risk devices can be closely monitored.

Population analysis module 504 uses the data collected in the database module 114 to manage the health of a population. For example, a clinic managing cardiac patients can access the APM system 100 and thereby obtain device-supplied advance information to predict and optimize resource allocation both as to immediate care and as a predictive metric for future need of practicing specialists. As another example, the spread of disease in remote populations can be localized and quarantined rapidly before further spread.

In one embodiment of the invention, the host 112 may be used as a "data clearinghouse," to gather and integrate data collected from the devices 102, 104, and 106, as well as data from sources outside the APM system 100, such as the external database 600. The integrated data can be shared with other interested entities, subject to privacy restrictions, thereby increasing the quality and integration of data available.

Learning module 506 analyzes the data provided from the various information sources, including the data collected by the advanced patient system 100 and external information sources. For example, the learning module 506 analyzes historical symptoms, diagnoses, and outcomes along with time development of the diseases and co-morbidities. The learning module 506 can be implemented via a neural network (or equivalent) system.

The learning module 506 can be partially trained (i.e., the learning module 506 may be implemented with a given set of preset values and then learn as the APM system functions) or untrained (i.e., the learning module 506 is initiated with no preset values and must learn from scratch as the APM system functions). In other alternative embodiments, the learning module 506 may continue to learn and adjust as the APM system functions (i.e., in real time), or the learning module 506 may remain at a given level of learning and only advanced to a higher level of understanding when manually allowed to do so.

The example learning module 506 uses various algorithms and mathematical modeling such as, for example, trend and statistical analysis, data mining, pattern recognition, cluster analysis, neural networks and fuzzy logic. Learning module 506 may perform deterministic and probabilistic calculations. Deterministic calculations include algorithms for which a clear correlation is known between the data analyzed and a given outcome. For example, there may be a clear correlation between the energy left in a battery of an implantable device and the amount of time left before the battery must be replaced.

A probabilistic calculation involves the correlation between data and a given outcome that is less than 100 percent certain. Probabilistic determinations require an analysis of several possible outcomes and an assignment of probabilities for those outcomes (e.g., an increase in weight of a patient may, at a 25% probability, signal an impending de-compensation event and/or indicate that other tests are needed). The learning module 506 performs probabilistic calculations and selects a given response based on less than a 100% probability. Further, as the learning module 506 "learns" for previous determinations (e.g., through a neural network configuration), the learning module 506 becomes more proficient at assigning probabilities for a given data pattern, thereby being able to more confidently select a given response. As the amount of data that has been analyzed by the learning module 506 grows, the learning module 506 becomes more and more accurate at assigning probabilities based on data patterns. A bifurcated analysis may be performed for diseases exhibiting similar symptoms. As progressive quantities of data are collected and the understanding of a given disease state advances, disease analysis is refined where a former singular classification may split into two or more sub-classes.

In addition, patient-specific clinical information can be stored and tracked for hundreds of thousands of individual patients, enabling a first-level electronic clinical analysis of the patient's clinical status and an intelligent estimate of the patient's short-term clinical prognosis. The learning module 506 is capable of tracking and forecasting a patient's clinical status with increasing levels of sophistication by measuring a number of interacting co-morbidities, all of which may serve individually or collectively to degrade the patient's health. This enables learning module 506, as well as caregivers, to formulate a predictive medical response to oncoming acute events in the treatment of patients with chronic diseases such as heart failure, diabetes, pain, cancer, and asthma/COPD, as well as possibly head-off acute catastrophic conditions such as MI and stroke.

Delivery module 118 coordinates the delivery of feedback based on the analysis performed by the host 112. In response to the analysis module 116, delivery module 118 can manage the devices 102, 104, and 106, perform diagnostic data recovery, program the devices, and otherwise deliver information as needed. In some embodiments, the delivery module 118 can manage a web interface that can be accessed by patients or caregivers. The information gathered by an implanted device can be periodically transmitted to a web site that is securely accessible to the caregiver and/or patient in a timely manner. In other embodiments, a patient accesses detailed health information with diagnostic recommendations based upon analysis algorithms derived from leading health care institutions.

In an alternative embodiment, the data collected and integrated by the advanced patient system 100, as well as any analysis performed by the system 100, is delivered by delivery module 118 to a caregiver's hospital computer system for access by the caregiver. A standard or custom interface facilitates communication between the APM system 100 and a legacy hospital system used by the caregiver so that the caregiver can access all relevant information using a system familiar to the caregiver.

The APM system 100 can also be configured so that various components of the system (e.g., ITU 108, communication system 110, and/or host 112) provide reporting to various individuals (e.g., patient and/or caregiver). For example, different levels of reporting can be provided by (1) the ITU 108 and (2) the host 112. The ITU 108 may be configured to conduct rudimentary analysis of data gathered from devices 102, 104, and 106, and provide reporting should an acute situation be identified. For example, if the ITU 108 detects that a significant heart arrhythmia is imminent or currently taking place, the ITU 108 provides reporting to the patient in the form of an audible or visual alarm.

The host 112 can provide a more sophisticated reporting system. For example, the host 112 can provide exception-based reporting and alerts that categorize different reporting events based on importance. Some reporting events do not require caregiver intervention and therefore can be reported automatically. In other escalating situations, caregiver and/or emergency response personnel need to become involved.

In addition to forms of reporting including visual and/or audible information, the APM system 100 can also communicate with and reconfigure one or more of the devices 102, 104, and 106. For example, if device 102 is part of a cardiac rhythm management system, the host 112 can communicate with the device 102 and reconfigure the therapy provided by the cardiac rhythm management system based on the data collected from one or more of the devices 102, 104, and 106. In another embodiment, the delivery module 118 can provide to the ITU 108 recorded data, an ideal range for the data, a conclusion based on the recorded data, and a recommended course of action. This information can be displayed on the ITU 108 for the patient to review or made available on the peripheral device 109 for the patient and/or clinician to review.

V. Example APM System with Additional Trigger Event Identification Capabilities

Figure 4:
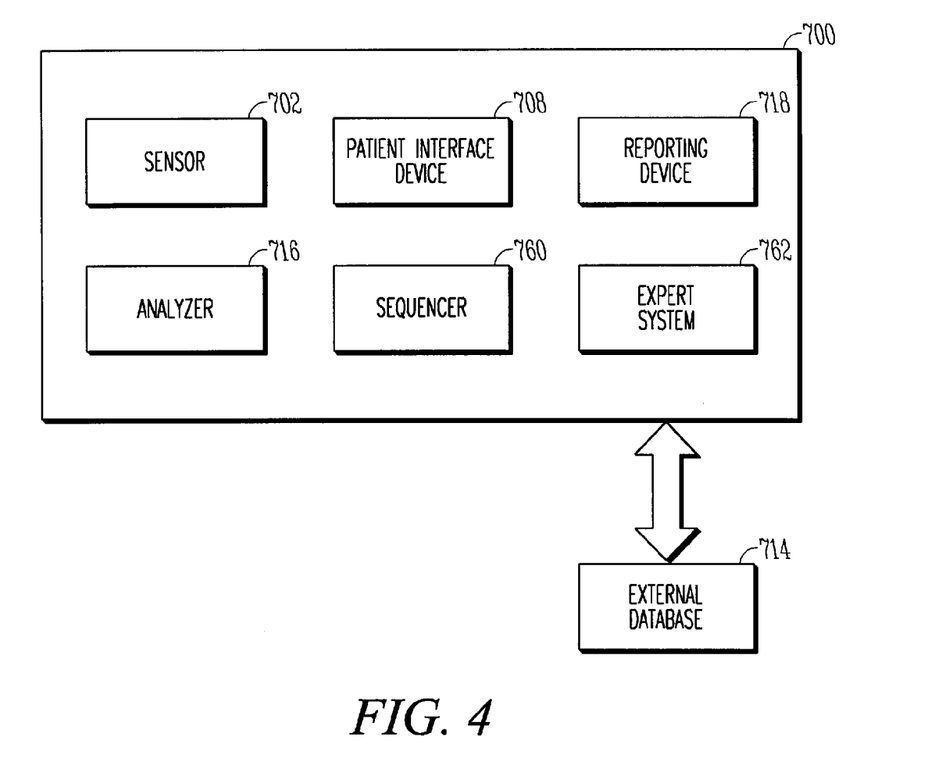
FIG. 4 illustrates an example automated system in accordance with the present invention.
Figure 5:
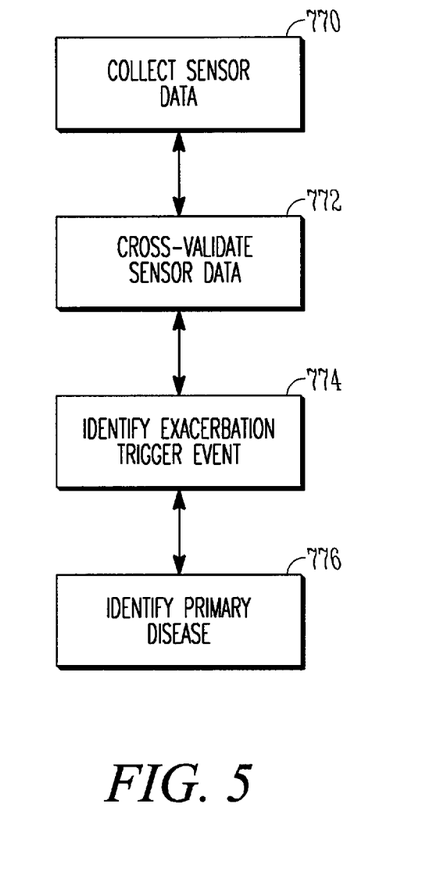
FIG. 5 illustrates an example schematic process diagram in accordance with the present invention.
Figure 6:
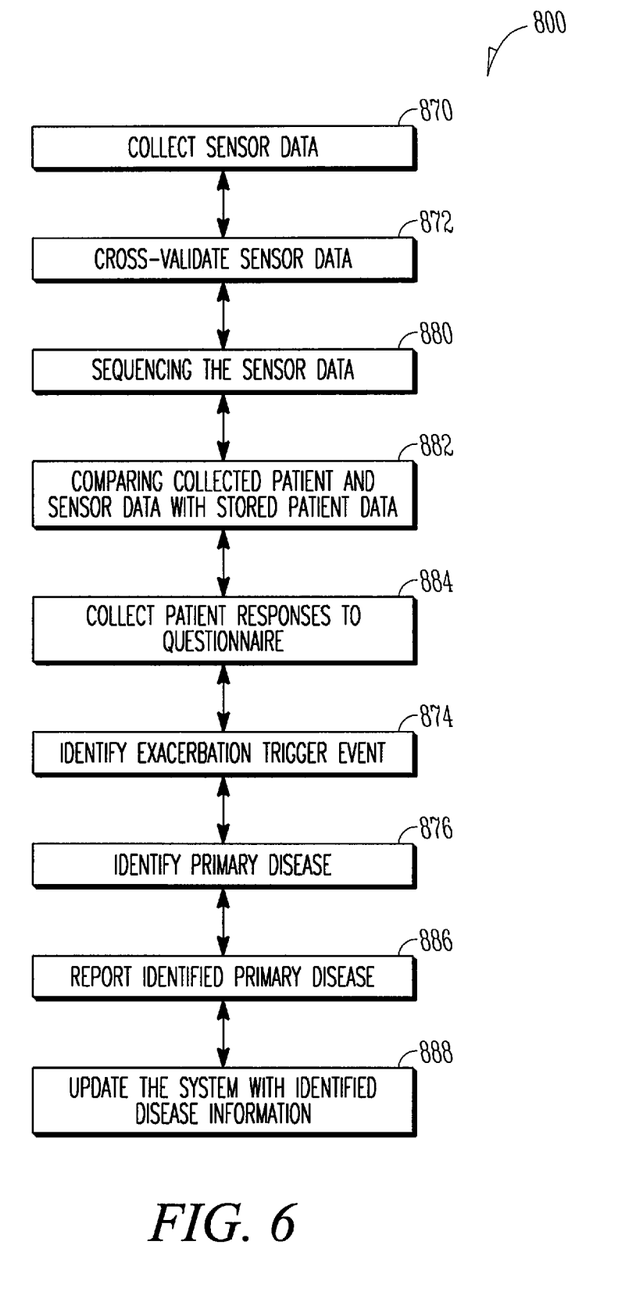
FIG. 6 illustrates another example schematic process diagram in accordance with the present invention.

An example automatic system 700 that can function independently or be incorporated into an advanced patient management system, such as system 100 described above, is shown and described with reference to FIGS. 4-6. System 700 includes a sensor 702, a patient interface 708, a reporting device 718, an analyzer 716, an expert system 762, a sequencer 760, and an external database 714. Together these features may provide functionality in accordance with the method steps shown in FIG. 5, namely, collect sensor data 770, cross-validate sensor data 772, identify exacerbation trigger event 774, and identify primary disease 776. Additional details related to the functions of the individual features and functions of system 700 are provided below and with reference to FIG. 6.

The sensor 702 may be equivalent to any of the devices 102, 104, 106 described above for APM 100. For example, sensor 702 can be an implantable device or external device that provides at least one of the following functions with respect to a patient in addition to other possible functions: (1) sensing/measuring, (2) data analysis, (3) therapy, (4) distribution of product, and (5) communication. For example, in one embodiment, sensor 702 is either an implanted or an external device used to sense or measure a variety of physiological, subjective, and environmental conditions of a patient using electrical, mechanical, and/or chemical means. The sensor 702 may be configured to automatically gather data or can require manual intervention by the patient. The sensor 702 may be positioned external and separated from the patient, positioned on an external surface of the patient, or positioned within the patient as an implanted device or sensor. The sensor 702 may be configured to store data related to the physiological and/or subjective measurements and/or transmit the data to a communication system (see, for example, communication system 110 in FIG. 1) using a variety of methods. Although only one sensor 702 is illustrated in FIG. 4, more or fewer sensors or related devices may be used for a given patient.

The analyzer 716 may provide much of the same functionality as the analysis module 116 described above. The analyzer 716 may be an independent module or a device that is integrated into other features of system 700. Analyzer 716 may include a patient analysis module, a device analysis module, a population analysis module, a learning module (see, for example, features 500, 502, 504 and 506 in FIG. 1), along with other features that utilize information collected by the system 700, as well as information for other relevant sources, to analyze data related to a patient and provide assessments of the patient's condition.

In performing analysis, the analyzer 716 may utilize data collected from a variety of sources, such as, for example, patient specific physiological and subjective data collected by the system 700, medical and historical records (e.g., lab test results, histories of illnesses, etc., drugs currently and previously administered, etc.), as well as information related to population trends provided from external database 714. Analyzer 716 preferably at least has the ability to cross-correlate data provided by sensor 702 to validate the data. Data validation can be performed in a number of ways, for example, by comparing concurrently collected data by multiple sensors (including sensor 702) that correspond to related data. Another cross-correlation method may involve comparison of current data from one or more sensors 702 with data collected previously by the one or more of the sensors 702. A still further example cross-correlation method may include comparison of current data with data provided by alternative databases, such as, for example, family health or medical history, clinical trials, guidelines, and environmental data databases that are stored or accessed via the external database 714.

By comparing collected data with other data that relates to the collected data, the collected data can be validated for accuracy and correctness thereby providing improved accuracy and correctness of the system 700 results. Cross-correlation with analyzer 716 may also be a means of determining if the devices 102, 104, 106 are functioning properly or are in need of further evaluation and testing to verify proper performance. As a result, early degradation or imminent failure of implanted devices can be identified and proactively addressed, or at-risk devices can be monitored.

The sequencer 760 can sequence the data provided by sensor 702 and/or prioritize the provided data based on, for example, order of relative importance as determined by, for example, a physician or system administrator, the chronology of data collection, the relative volume of data, or groupings of data related to certain physiological parameters. Sequencing of data may be particularly useful for prioritizing what may otherwise be amounts of information that are too large for useful automatic analysis by the analyzer 716 or more manual analysis by an administrator of the system 700 (e.g., a physician or technician).

In some embodiments, analyzer 716, and sequencer 760 may be integrated into an ITU or a host of an APM system, or may be integrated into the sensor 702, a remote periphery device, or other feature of the APM system.

The patient interface device 708 may include some or all of the functionality described above related to ITU 108, or may be configured more generically as a purely patient interface device, or to include some of the features described above related to devices 102, 104, 106. For example, device 708 may be well suited for collecting subjective data; that is, information related to a patient's feelings, perceptions, and/or opinions, as opposed to objective physiological data. For example, the "subjective" devices can measure patient responses to inquiries such as "How do you feel?" and "How is your pain?" The device can prompt the patient and record subjective data from the patient using visual and/or audible cues such as, for example, pressing buttons on a keypad, or by audible communication using a speaker and a microphone.

In one example embodiment, the device 708 presents the patient with a relatively small number of responses to each question posed to the patient. For example, the responses available to the patient may include three faces representing feelings of happiness, nominalness, and sadness. Averaged over time, a trend of a patient's well being will emerge from the patient's choices, and a trigger event for future patient health exacerbation can be more clearly identified.

The subjective data can be collected from the patient at set times, or, alternatively, collected whenever the patient chooses to provide subjective data. The subjective data can also be collected simultaneously with physiological data to provide greater insight into overall patient wellness. The device 708 can be any device that accepts input from a patient or other concerned individual and/or provides information in a format that is recognizable to the patient.

The data provided by the sensor 702, patient interface device 708, and other features of system 700 may be used as inputs to an adaptable scenario for improved communications with the patient. For example, the patient inputs to the patient interface device 708 may be used to determine what additional inquiries the device 708 may pose to the patient. These additional inquiries may be further personalized in view of other data provided by, for example, current or past measured data from the sensor 702.

The reporting device 718 may provide many of the same or similar functions as the delivery module 118 described above. For example, the information gathered by an implanted device (e.g., sensor 702) can be periodically transmitted to a web site that is securely accessible to the caregiver and/or patient in a timely manner via the reporting device 718. In other embodiments, a patient accesses detailed health information with diagnostic recommendations based upon analysis algorithms derived from leading health care institutions via the reporting device 718. In an alternative embodiment, the data collected and verified by system 700, as well as any analysis performed by the system 700, is delivered by reporting device 718 to a caregiver's hospital computer system for access by the caregiver. A standard or custom interface facilitates communication between the system 700 and a legacy hospital system used by the caregiver via the reporting device 718 so that the caregiver can access all relevant information using a system familiar to the caregiver.

The reporting device may also be configured to provide communication between various components of the system 700 (e.g., patient interface device 708, sensor 702, analyzer 716 and sequencer 760), and between those components and various individuals at remote or local locations (e.g., patient and/or caregiver). For example, if the system 700 detects that a threatening heart arrhythmia is imminent or currently taking place, the patient interface 708 can provide reporting to the patient in the form of an audible or visual alarm before administering therapy and reporting to the caregiver via the reporting device 718.

Reporting device 718 may also be configured to, for example, categorize different reporting events based on importance or to report summaries of specific co-morbidities and physiological occurrences at predetermined time intervals. Some reporting events do not require caregiver intervention and therefore can be reported automatically. In other escalating situations, caregiver and/or emergency response personnel need to become involved.

The expert system 762 may be any commercially available or highly specialized system that is capable of inputting information from various sources (e.g., collected data from the sensor 702, validated data from the analyzer 716, sequenced data from sequencer 760, related data from the external database 714), performing analysis of the inputted information, and determining a primary patient disease. The expert system 762 may be a diagnosis system that uses an algorithm to eliminate diseases that are less probable and determine a few most probable scenarios for potential diseases based on, for example, certain probabilities given the patient related inputs (e.g., physiological indicators, patient subjective response, past medical history, etc.) to the system 762. In some embodiments, the expert system 762 may also be capable of performing additional analysis for determining a trigger event to the resulting determined patient disease or patient health related exacerbation.

The reporting device 718 may be used to report results from the expert system 762 to a caregiver (e.g., physician, nurse, or technician) who evaluates the results in view of other patient related data and provides a caregiver diagnosis. The caregiver diagnosis may be reported back to the expert system to be used as a means of system learning. System learning involves a confirmation whether the expert system diagnosis was correct, and if not correct, storage of the actual caregiver diagnosis for purposes of future diagnosis by the expert system. Thus, the expert system 762 can be a changing system that is adaptable for a particular patient.

Some embodiments of system 700 may not include the reporting device 718, expert system 762, or other features described above with reference to FIG. 4. In such embodiments, system 700 may be most useful for automatically gathering, validating, and communicating data related to the patient's health condition for the primary purpose of identifying a trigger event to a patient related health exacerbation after the exacerbation has occurred. For example, a patient might have developed diabetes. If poorly controlled, this disease could lead to cardiomyopathy and left ventricular (LV) hypertrophy. When diagnosis of heart failure is identified it is important to treat the primary disease that lead to the heart failure.

Another method of use 800 related to the system 700 is shown and described with reference to FIG. 6. Method 800 includes some of the same steps described above with reference to FIG. 5. Method 800 may include collecting sensor data 870, cross-validating senor data 872, sequencing the sensor data 880, comparing collected patient and sensor data with stored patient related data 882, and collecting patient response to a questionnaire 884. Method 800 may also include identifying an exacerbation trigger event 874, identifying a primary disease 876, reporting the identified primary disease 886, and updating the system with the identified disease information. In other embodiments, method 800 may include additional or fewer steps and features to those shown in FIG. 6. For example, in addition to the reporting step 886, the method may also include reporting of the cross-validated data and the collected patient responses to a caregiver on a periodic basis.

VI. Conclusion

One or more headings have been provided above to assist in describing the various embodiments disclosed herein. The use of headings and the resulting division of the description by the headings should not be construed as limiting in any way. The subject matter described under one heading can be combined with subject matter described under one or more of the other headings without limitation and as desired.

The systems and methods of the present disclosure can be implemented using a system as shown in the various figures disclosed herein including various devices and/or programmers, including implantable or external devices. Accordingly, the methods of the present disclosure can be implemented: (1) as a sequence of computer implemented steps running on the system; and (2) as interconnected modules within the system. The implementation is a matter of choice dependent on the performance requirements of the system implementing the method of the present disclosure and the components selected by or utilized by the users of the method. Accordingly, the logical operations making up the embodiments of the method of the present disclosure described herein can be referred to variously as operations, steps, or modules. It will be recognized by one of ordinary skill in the art that the operations, steps, and modules may be implemented in software, in firmware, in special purpose digital logic, analog circuits, and any combination thereof without deviating from the spirit and scope of the present invention as recited within the claims attached hereto.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A method for determining a primary source of exacerbation of a health of a patient having a chronic illness, the method comprising the steps of:
    collecting sensor data indicative of at least one patient physical condition;
    cross-correlating the collected sensor data to validate the collected data;
    collecting patient responses to an interactive questionnaire;
    identifying a trigger event for a patient health exacerbation based on the collected data and patient responses,
    wherein the trigger event is determined by a neural-network-based learning module in a computer;
    identifying a primary disease associated with the trigger event using an expert system;
    and
    reporting the identified primary disease and the primary source of the exacerbation to a caregiver.

2. The method of claim 1, further comprising validating the identified primary disease and trigger event by a caregiver.

3. The method of claim 2, further comprising updating the expert system with information related to the validated primary disease and trigger event.

4. The method of claim 1, further comprising sequencing the collected data.

5. The method of claim 1, wherein cross-correlation of the collected data includes comparing the collected data with data collected from another patient sensor.

6. The method of claim 1, wherein cross-correlation of the collected data includes comparing the collected data with stored patient data.

7. The method of claim 6, wherein the stored patient data includes information selected from the group consisting of the patient's family health history, the patient's previous health history, a pharmaceutical database that contains information related to pharmacodynamics, drug side effects, drug compatibility, and pharmacogenomics, clinical trials, environmental conditions, physician guidelines, and population trends.

8. The method of claim 1, further comprising generating an abnormality signal if cross-correlation of the collected sensor data indicates an abnormality.

9. The method of claim 8, further comprising responding to the abnormality signal with a report provided to the patient or to a caregiver.

10. The method of claim 1, wherein the interactive questionnaire includes questions related to an adaptable scenario.

11. The method of claim 1, further comprising verifying the primary disease.

12. The method of claim 11, wherein the cross-correlation is performed with an analyzer, and the method further includes reporting verification of the primary disease to the analyzer to aid in system learning.

13. An automated system configured to determine a primary source of patient health-related exacerbation, the system comprising:
at least one sensor to collect data related to the patient health-related exacerbation;
an analyzer to validate the collected data;
a patient interface device to receive patient inputs to at least one question;
an identifier device to receive the patient inputs and collected data and to identify a trigger event for a patient health-related exacerbation,
wherein the identifier device includes a neural network-based learning module; and
an expert system configured to receive the patient inputs and the collected data and identify a primary patient disease.

14. The system of claim 13, further comprising a reporting device configured to generate reports related to the identified primary patient disease, patient inputs, and sensed patient conditions.

15. The system of claim 14, wherein the reports are used by the identifier device to determine the primary source.

16. The system of claim 13, further comprising a sequencer configured to sequence the collected data.

17. The system of claim 16, wherein the sequencer initiates sequencing in response to a predetermined patient input or a cross-correlation result from the analyzer, 18. The system of claim 13, wherein the patient interface device includes at least one of a keypad, touch control screen or other input device.

19. The system of claim 18, wherein the patient interface device is configured to present a series of questions in the form of a questionnaire, the questionnaire being structured as an adaptable scenario.

20. The system of claim 13, wherein the analyzer is configured to receive verification of the identified primary disease to aid in a learning function of the analyzer.

21. The system of claim 13, wherein the analyzer cross-correlates the sensed data with data from another patient sensor.

22. The system of claim 13, wherein the analyzer cross-correlates the sensed data with stored patient data sensed previously.

23. The system of claim 13, wherein the analyzer cross-correlates the sensed data with data related to the patient's family health history, a pharmaceutical database that contains information on pharmacodynamics, drug side effects, drug compatibility, and pharmacogenotnics, clinical trials, environmental conditions, and guidelines.

24. The system of claim 13, wherein the analyzer is configured to detect abnormalities in the at least one sensor resulting from the cross-correlation.

25. A method of automatically determining a primary patient disease that causes a patient health-related exacerbation, the method comprising the steps of:
collecting sensor data indicative of at least one patient physical condition;
cross-correlating the collected sensor data to validate the collected data;
collecting patient responses to an interactive questionnaire; and
determining the primary patient disease using an expert computer system, the validated collected data, and the patient responses, wherein the primary patient disease is determined by a neural network-based learning module in the computer system and wherein determining the primary patient disease includes determining two or more disease subclasses.

26. The method of claim 25, further comprising the step of determining a primary source of health exacerbation based on the collected data, the patient responses, and the determined patient disease.

* * * * *